US010294944B2

(12) United States Patent
Aber et al.

(10) Patent No.: US 10,294,944 B2
(45) Date of Patent: May 21, 2019

(54) FLOW THRU MECHANICAL BLOOD PUMP BEARINGS

(71) Applicant: EVERHEART SYSTEMS INC., Webster, TX (US)

(72) Inventors: Greg S. Aber, Houston, TX (US); Allan S. Rhoades, Fort Worth, TX (US)

(73) Assignee: EVERHEART SYSTEMS INC., Webster, TX (US)

( * ) Notice: Subject to any disclaimer, the term of this patent is extended or adjusted under 35 U.S.C. 154(b) by 347 days.

(21) Appl. No.: 13/790,239

(22) Filed: Mar. 8, 2013

(65) Prior Publication Data

US 2014/0255225 A1  Sep. 11, 2014

(51) Int. Cl.
*F04D 13/06* (2006.01)
*F04D 13/02* (2006.01)
(Continued)

(52) U.S. Cl.
CPC .......... *F04D 13/06* (2013.01); *A61M 1/1036* (2014.02); *F04D 13/024* (2013.01);
(Continued)

(58) Field of Classification Search
CPC .. F04D 13/024; F04D 13/026; F04D 13/0633; F04D 25/062; F04D 29/0465; F04D 29/20; F04D 26/263; F04D 29/266; F04D 29/041; F04D 29/042; F04D 29/046–29/047; F04D 29/186; F04D 29/2266; F04D 13/06; A61M 1/1013; A61M 1/1017; A61M 1/1025;
(Continued)

(56) References Cited

U.S. PATENT DOCUMENTS 4,643,641 A    2/1987  Clausen et al.
4,984,972 A    1/1991  Clausen et al.
(Continued)

FOREIGN PATENT DOCUMENTS

EP         1113177 A2     7/2001
WO    WO-92/21388 A1    12/1992
(Continued)

OTHER PUBLICATIONS

Lawrence Pumps. "Run Times", col. 2, Issue No. 1, Jan. 2005.
(Continued)

*Primary Examiner* — Essama Omgba
*Assistant Examiner* — Charles Nichols
(74) *Attorney, Agent, or Firm* — Nathan S. Smith; Mark I. Bentley; Morgan, Lewis & Bockius LLP (57) ABSTRACT

A flow thru mechanical bearing system can be used in an implantable rotary blood pump that includes a pump housing. An impeller housed in the pump housing can be radially supported by a row of at least three low friction contact points located on an inside bore of the impeller. The impeller may be axially supported by a second mechanical bearing. The second mechanical bearing may provide at least three axial contact points on the top surfaces of the impeller. The impeller is driven by a magnetic coupling which functions mainly to transmit torque to the impeller. Further, in some cases, the magnetic coupling may restrain axial motion of the impeller.

23 Claims, 7 Drawing Sheets

(51) Int. Cl.
*A61M 1/10* (2006.01)
*F04D 29/047* (2006.01)
*A61M 1/12* (2006.01)

(52) U.S. Cl.
CPC .......... *F04D 29/047* (2013.01); *A61M 1/101* (2013.01); *A61M 1/1031* (2014.02); *A61M 1/122* (2014.02); *F04D 13/0633* (2013.01)

(58) Field of Classification Search
CPC .... A61M 1/101; A61M 1/122; A61M 1/1031; A61M 1/1036
See application file for complete search history.

(56) References Cited

U.S. PATENT DOCUMENTS

| | | | |
|---|---|---|---|
| 5,017,103 A | | 5/1991 | Dahl |
| 5,049,134 A | | 9/1991 | Golding et al. |
| 5,290,227 A | | 3/1994 | Pasque |
| 5,370,509 A | | 12/1994 | Golding et al. |
| 5,611,679 A | | 3/1997 | Ghosh et al. |
| 5,890,883 A | | 4/1999 | Golding et al. |
| 5,947,703 A | * | 9/1999 | Nojiri et al. .................. 417/420 |
| 6,015,272 A | | 1/2000 | Antaki et al. |
| 6,048,363 A | | 4/2000 | Nagyszalanczy et al. |
| 6,071,093 A | | 6/2000 | Hart |
| 6,158,984 A | | 12/2000 | Cao et al. |
| 6,181,040 B1 | | 1/2001 | Schob |
| 6,227,797 B1 | | 5/2001 | Watterson et al. |
| 6,234,772 B1 | | 5/2001 | Wampler et al. |
| 6,302,910 B1 | | 10/2001 | Yamazaki et al. |
| 6,445,956 B1 | | 9/2002 | Laird et al. |
| 6,547,530 B2 | | 4/2003 | Ozaki et al. |
| 6,589,031 B2 | * | 7/2003 | Maeda et al. ................ 417/420 |
| 6,808,371 B2 | * | 10/2004 | Niwatsukino et al. ....... 417/353 |
| 6,894,456 B2 | | 5/2005 | Tsukamoto et al. |
| 7,189,260 B2 | | 3/2007 | Horvath et al. |
| 7,616,997 B2 | | 11/2009 | Kieval et al. |
| 7,682,301 B2 | | 3/2010 | Wampler et al. |
| 7,699,586 B2 | | 4/2010 | LaRose et al. |
| 7,976,271 B2 | * | 7/2011 | LaRose ................ A61M 1/101 415/104 |
| 8,114,008 B2 | | 2/2012 | Hidaka et al. |
| 8,551,163 B2 | | 10/2013 | Aber et al. |
| 8,901,775 B2 | | 12/2014 | Armstrong et al. |
| 2002/0076322 A1 | * | 6/2002 | Maeda ................ F04D 29/0467 415/170.1 |
| 2003/0091249 A1 | | 5/2003 | Kurimura et al. |
| 2003/0124007 A1 | | 7/2003 | Schima et al. |
| 2003/0175119 A1 | | 9/2003 | Tajima et al. |
| 2004/0236420 A1 | | 11/2004 | Yamane et al. |
| 2005/0025630 A1 | * | 2/2005 | Ayre ..................... A61M 1/101 417/53 |
| 2005/0095151 A1 | | 5/2005 | Wampler et al. |
| 2005/0178526 A1 | * | 8/2005 | Naganawa .............. F04D 9/007 165/80.2 |
| 2005/0281685 A1 | | 12/2005 | Woodard et al. |
| 2005/0287022 A1 | | 12/2005 | Yaegashi et al. |
| 2006/0155159 A1 | | 7/2006 | Melvin |
| 2006/0245955 A1 | * | 11/2006 | Horiuchi et al. ............. 417/420 |
| 2007/0280841 A1 | * | 12/2007 | LaRose ................ A61M 1/101 417/423.12 |
| 2008/0124231 A1 | | 5/2008 | Yaegashi |
| 2008/0269880 A1 | | 10/2008 | Jarvik |
| 2009/0112626 A1 | | 4/2009 | Talbot et al. |
| 2009/0234447 A1 | | 9/2009 | LaRose et al. |
| 2009/0270679 A1 | | 10/2009 | Hoeg et al. |
| 2010/0045114 A1 | | 2/2010 | Sample |
| 2010/0063347 A1 | | 3/2010 | Yomtov |
| 2010/0164296 A1 | | 7/2010 | Kurs |
| 2010/0185280 A1 | | 7/2010 | Ayre et al. |
| 2011/0188996 A1 | | 8/2011 | Hoshi et al. |
| 2011/0238172 A1 | | 9/2011 | Akdis |
| 2012/0089225 A1 | | 4/2012 | Akkerman et al. |
| 2012/0280305 A1 | | 11/2012 | Zhu et al. |
| 2013/0241306 A1 | | 9/2013 | Aber et al. |
| 2013/0345493 A1 | | 12/2013 | Aber et al. |
| 2014/0200664 A1 | | 7/2014 | Akkerman et al. |
| 2015/0061591 A1 | | 3/2015 | Armstrong et al. |

FOREIGN PATENT DOCUMENTS

| | | |
|---|---|---|
| WO | WO-2009/091267 | 7/2009 |
| WO | WO-2009/104451 A1 | 8/2009 |

OTHER PUBLICATIONS

Zirkelback, et al., "Finite Element Analysis of Herringbone Groove Journal Bearings: A Parametric Study," Transactions of the ASME, Apr. 1998, pp. 234-240, vol. 120.

El-Moli, "Study of Parameters Influencing Design Factors of Oil-Lubricated Herringbone Grooved Journal Bearing," Post Graduate Thesis, Jan. 25, 2004.

Mielke, et al., "In vitro evaluation of a new resilient, hard-carbon, thin-film coating as a bearing material for ventricular assist devices," J. Biomedical Science and Engineering, 200, 3, 525-528.

John Crane, "Multilobe Bearings," Nov. 2008, 48 pages.

* cited by examiner

FIG. 1

FIG. 2
(SECTION A-A)

FIG. 3

(SECTION B - B)

FIG. 4
(DETAIL C)

FIG. 9
(SECTION D-D)

FIG. 10
(DETAIL E)

FLOW THRU MECHANICAL BLOOD PUMP BEARINGS

FIELD OF THE INVENTION

This invention relates to blood pump systems. More particularly, to bearings used in implantable rotary blood pumps.

BACKGROUND OF INVENTION

Implantable blood pumps can be utilized for total artificial heart replacement or ventricular assistance. Implantable blood pumps may be utilized for temporary or long term ventricular assistance or to permanently replace a patient's damaged heart. Some blood pumps may mimic the pulsatile flow of the heart. However, some blood pumps have progressed to designs that are non-pulsatile. Non-pulsatile blood pumps are typically rotary and propel fluid with impellers that span the spectrum from radial flow, centrifugal type impellers to axial flow, auger type impellers.

A common issue encountered by blood pumps is blood trauma. The causes of blood trauma can be partially attributed to shear stress and/or heat generated by the bearings supporting the impeller. Shear stress and/or heat may cause hemolysis, thrombosis, and the like. In some blood pumps, the impeller may be driven by a shaft. The shaft may be sealed off with shaft seals to prevent blood from entering undesirable areas, such as a motor driving the shaft. However, shaft seals generate excess heat that may produce blood clots, and shaft seals may fail and allow blood to enter unwanted areas. A great deal of effort has been devoted to reducing or eliminating blood trauma in rotary blood pumps. One solution to minimizing or eliminating blood trauma is to provide hydrodynamic support of the impeller. For example, hydrodynamic support may be provided by ramp, wedge, plain journal, multi-lobe or groove hydrodynamic bearings. Another solution is to provide mechanical support of the impeller using mechanical bearings, such as jewel type bearings in the form of a shaft and sleeve or ball and cup. These mechanical bearings may utilize biocompatible hard ceramic materials. To function properly in blood, a mechanical bearing must generate very little heat and should avoid stagnant or recirculating areas of blood flow to prevent the formation of blood clots. Another solution proposed is the utilization of passive permanent magnetic and active controlled magnetic bearings to provide impeller support in blood pumps. Magnetic bearings, hydrodynamic bearings, and/or mechanical bearings may be combined to provide impeller support in blood pumps. However, magnetic bearing systems may require sensors and complex controls. Hydrodynamic bearings may require small clearances which may cause slow moving or stagnant blood flow between hydrodynamic bearing surfaces. Further, some blood pumps incorporate electric motors into the pumping chamber, rather than providing separate motor and pumping chambers. For example, a stator may be provided in the pump housing and magnets can be incorporated into an impeller to provide a pump impeller that also functions as the rotor of the electric motor.

The various embodiments discussed herein provide mechanical blood pump bearings that cause minimal blood trauma, generate very little heat from friction, and can be thoroughly washed by blood flow to prevent the formation of blood clots. Further, these bearing systems are simple and robust, without requiring complicated controls and sensors or small clearances.

SUMMARY OF THE INVENTION

The discussion herein provides a description of flow thru mechanical blood pump bearings that are energy efficient, cause minimal blood trauma, and are simple and robust.

In one embodiment, an impeller for a blood pump is radially supported by a first mechanical bearing that provides at least three contact points located on an inside bore surface of the impeller. In another embodiment, a second mechanical bearing may provide at least three contact points located on the top surfaces of an impeller to support the impeller axially. In yet another embodiment, the first mechanical bearing and the second mechanical bearing may be combined to provide contact points on an internal bore surface of an impeller and a top surface of an impeller to provide radial and axial support of the impeller.

In some embodiments, contact points may be formed from or coated with a biocompatible low friction material. In some embodiments, an impeller may be magnetically coupled to a driver or motor through a diaphragm of a pump housing.

The foregoing has broadly outlined various features of the present disclosure in order that the detailed description that follows may be better understood. Additional features and advantages of the disclosure will be described hereinafter.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein.

DETAILED DESCRIPTION

Refer now to the drawings wherein depicted elements are not necessarily shown to scale and wherein like or similar elements are designated by the same reference numeral through the several views.

Referring to the drawings in general, it will be understood that the illustrations are for the purpose of describing particular implementations of the disclosure and are not intended to be limiting thereto. While most of the terms used herein will be recognizable to those of ordinary skill in the art, it should be understood that when not explicitly defined, terms should be interpreted as adopting a meaning presently accepted by those of ordinary skill in the art.

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

Implantable blood pumps utilize a variety of different methods to support impellers, such as mechanical, hydrodynamic, and magnetic bearings. Mechanical bearings can generate heat that can cause blood trauma resulting in blood clots or hemolysis. Hydrodynamic bearings may require small clearances for the bearing to properly operate. Magnetic bearings may utilize sensors and/or complex controls.

An improved mechanical bearing system for a blood pump is discussed herein. A flow thru mechanical blood pump bearing system may cause minimal blood trauma, generate very little heat from friction, and can be thoroughly washed by blood flow to prevent the formation of blood clots. Further, these bearing systems are simple and robust, without requiring complicated controls and sensors, such as used in active magnetic bearing systems, or small clearances, such as used in some hydrodynamic bearing systems.

Mechanical bearing systems discussed herein may be utilized in a variety of blood pump systems. A blood pump system may include a housing, an inlet for receiving blood, an impeller for aiding blood flow, a driver that rotates the impeller, and an outlet for outputting blood. Blood pump systems may utilize radial or axial flow impellers. In some embodiments, the driver may be a motor and shaft coupled to the impeller. In other embodiments, the driver may be a magnetic coupling that rotates the impeller. In some embodiments, other mechanical bearings, hydrodynamic bearings, magnetic bearings, or a combination thereof may be utilized in conjunction with the mechanical bearing system discussed herein. In some embodiments, a mechanical blood pump bearing system may be capable of operating for extended periods (e.g. ≥5 years) with minimal mechanical wear and low friction.

While the embodiments of mechanical bearing systems discussed herein may refer to specific types of blood pumps, including particular housing, inlet, impeller, driver, or outlet designs, it will be recognized that such discussion is provided for illustrative purposes only.

Figure 1:
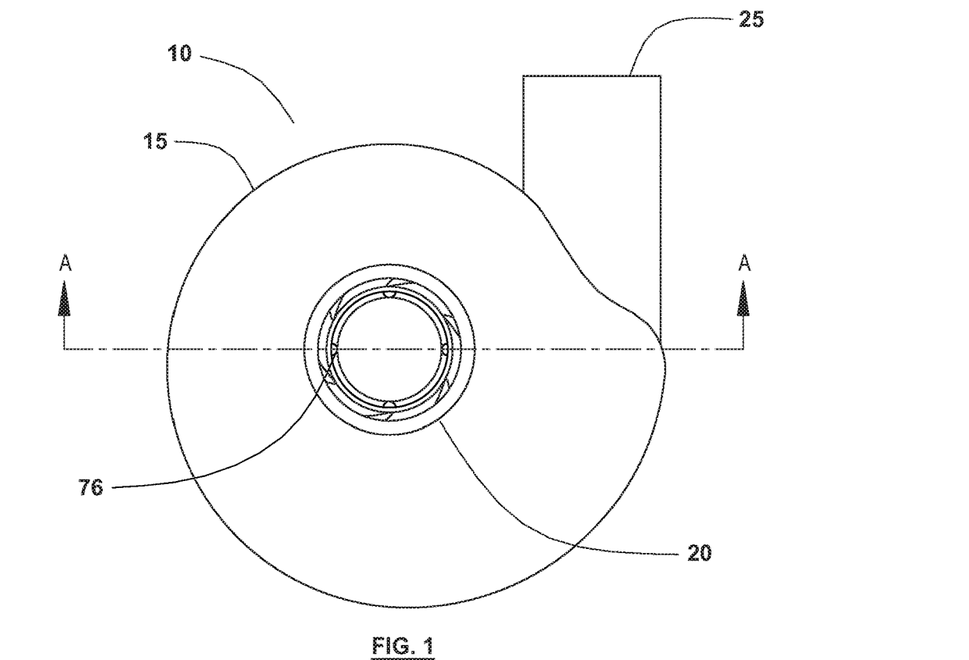
FIG. 1 is a top view of an illustrative embodiment of a pump.
Figure 2:
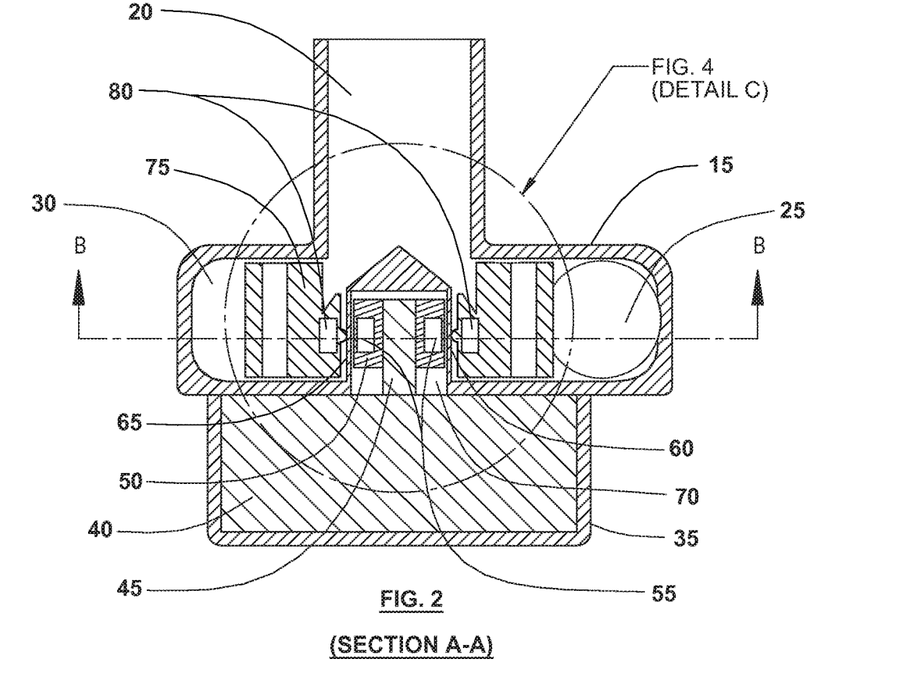
FIG. 2 is a cross-sectional side view of an illustrative embodiment of a pump with a radial mechanical bearing.

FIG. 1 is a top view of an illustrative embodiment of pump 10. Pump 10 is formed from pump housing 15 providing inlet 20 and outlet 25. Pump housing 15 may be composed of two or more pieces and may be joined by welding. In other embodiments, pump housing 15 may be joined by fusing, press fit, threading, screw and elastomeric sealing, bonding, fasteners, any other suitable joining method or combinations thereof. Line A-A passing through pump housing 15 indicates the plane from which the cross-sectional view in FIG. 2 is provided. FIG. 2 is a cross-sectional side view of an illustrative embodiment of pump 10. Motor housing 35 may be joined to pump housing 15 by welding, fusing, press fit, threading, screw and elastomeric sealing, bonding, fasteners, any other suitable joining method or combinations thereof. Pump housing 15 provides impeller chamber 30 for impeller 75. Impeller chamber 30 has inlet 20 for connection to a fluid source and outlet 25 for providing fluid to a desired location. Impeller chamber 30 may be sealed and pressure tight to prevent fluid from entering/exiting impeller chamber 30 from locations other than inlet 20 and outlet 25.

Figure 7:
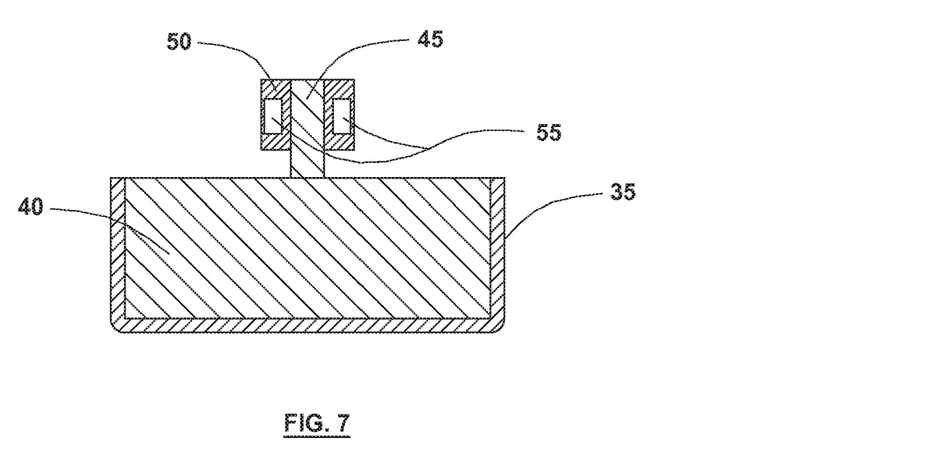
FIG. 7 is a cross-sectional view of an illustrative embodiment of a motor housing of a pump.

Motor housing 35 is attached to pump housing 15 to form a fluid and/or pressure tight chamber for motor 40. While motor housing 35 is shown as a separate component from pump housing 15, in other embodiments, pump housing 15 and motor housing 35 may be combined to form a single combined housing. A cross-sectional view of an illustrative embodiment of motor 40 and motor housing 35 of pump 10 is shown in FIG. 7. In particular, motor housing 35 is shown separate from pump housing 15. Motor 40 is entirely contained between pump housing 15 and motor housing 35. A high efficiency electric motor can be utilized, such as an electric motor with efficiency of about 85% or greater. However, in other embodiments, any other suitable driving means can be utilized. Motor 40 provides shaft 45 with hub 50 mounted to shaft 45. Hub 50 contains one or more permanent magnets and/or magnetic materials 55. Motor 40 rotates shaft 45 causing permanent magnets 55 placed in hub 50 to rotate. In some embodiments, a motor with a useful life equal to or greater than 5 years is utilized.

Figure 4:
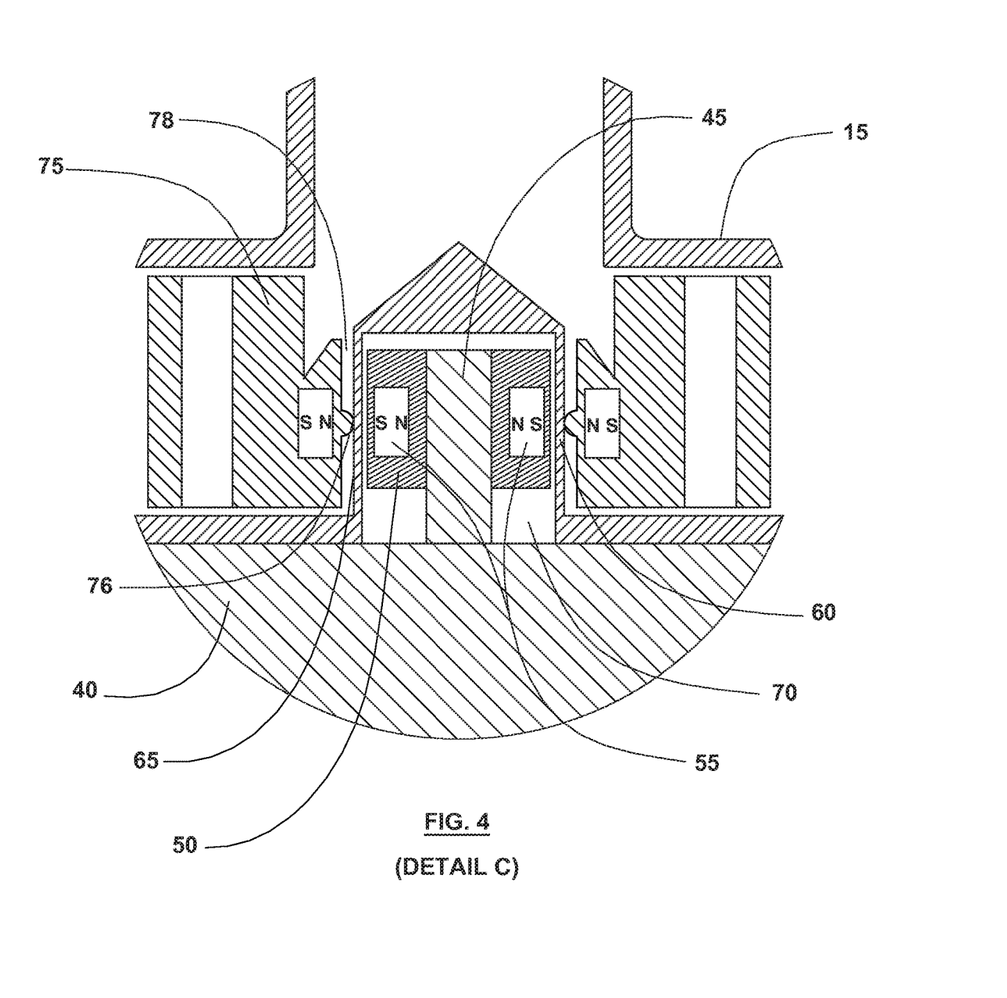
FIG. 4 is a close up cross-sectional view of an area of an illustrative embodiment of a pump thereof.
Figure 5:
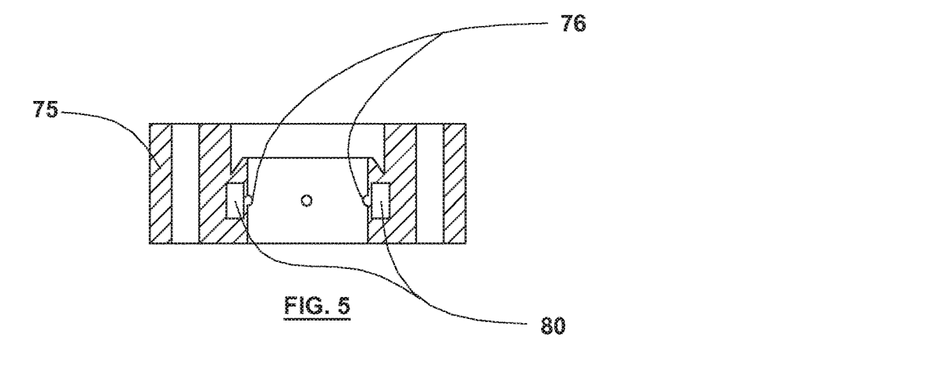
FIG. 5 is a cross-sectional view of an illustrative embodiment of an impeller.
Figure 6:
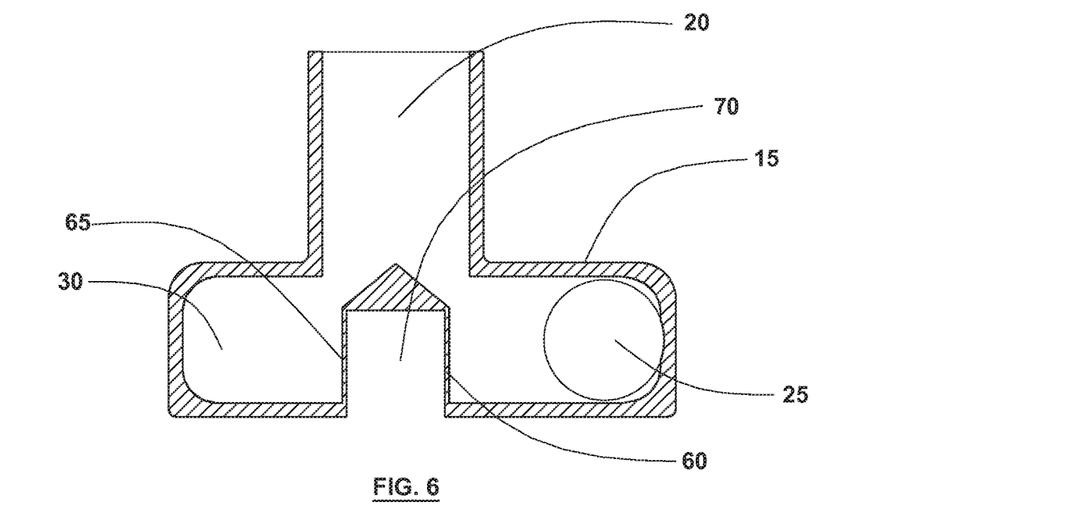
FIG. 6 is a cross-sectional view of an illustrative embodiment of a pump housing.

A cross-sectional view of an illustrative embodiment of pump housing 15 without impeller 75 is shown in FIG. 6. Pump housing 15 may provide a non-ferromagnetic and/or non-electrically conductive diaphragm 60 separating impeller chamber 30 from the chamber housing motor 40. Diaphragm 60 defines cavity 70 providing a region for hub 50 to rotate within. A cross-sectional view of an illustrative embodiment of impeller 75 is shown in FIG. 5. Impeller 75 includes one or more permanent magnets and/or magnetic materials 80. Permanent magnets 80 allow impeller 75 to be magnetically coupled to hub 50. This magnetic coupling allows motor 40 to cause impeller 75 to rotate when motor 40 rotates hub 50. FIG. 4 is a close up cross-sectional view of an area C (see FIG. 2) of an illustrative embodiment of pump 10. Diaphragm 60 may provide cylindrical bearing surface 65 for impeller 75 to rotate around. An internal bore of impeller 75 provides at least three contact points 76 protruding from the internal bore surface that may contact cylindrical bearing surface 65. Contact points 76 may be referred to as radial contact points since radial loads are supported by these contact points. While the nonlimiting embodiment shown utilizes four contact points 76, other embodiments may utilize three or more contact points. Contact points 76 may be semi-spherically shaped, semi-ellipsoid shaped, concave shaped, or the like. Contact points 76 may be nonconforming or conforming. In some embodiments, the curvature of contact points 76 matches the curvature of bearing surface 65. Contact points 76 may be equidistantly spaced around the internal bore surface of impeller 75 at an angle ($\alpha$) to provide balanced operation, wherein α represent an angle between two contact points 76 relative to the center of impeller 75. In the embodiment shown, the three contact points 76 are positioned at an equal height (h) from the bottom of impeller 75, which is referred to herein as a row. In other embodiments, one or more contact points 76 may be aligned at two or more different heights. In another embodiment, multiple sets of contact points 76 may be utilized, and each set may be arranged in two or more rows. In other embodiments, contact points 76 may be disposed on cylindrical bearing surface 65, rather than the internal bore of impeller 75.

The bearing surface 65 of diaphragm 60 may be coated with a biocompatible low friction coating, such as Diamond Like Carbon (DLC) or the like. Contact points 76 may also be coated with a biocompatible low friction coating, such as Diamond Like Carbon (DLC) or the like. In some embodiments, the contact points 76 may have a sliding Coefficient of Friction (COF) of 0.15 or less. The low friction coatings utilized on the bearing surface 65 and contact points 76 lower the amount of heat generated by friction. In other embodiments, bearing surface 65 and contact points 76 may be made from a hard biocompatible ceramic material, such as aluminum oxide, zirconium dioxide, silicon carbide, or silicon nitride.

Figure 11:
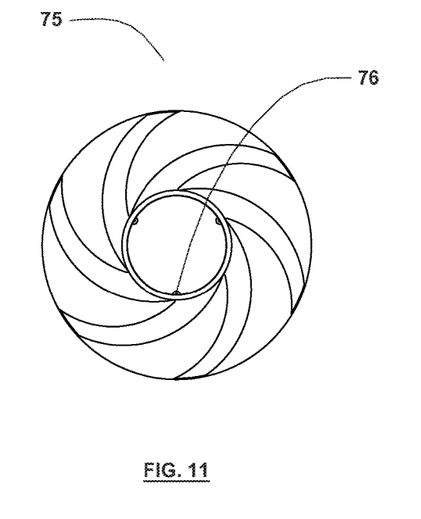
FIG. 11 and 12 are top and isometric views, respectively, of an illustrative embodiment of an impeller with a radial mechanical bearing.
Figure 12:
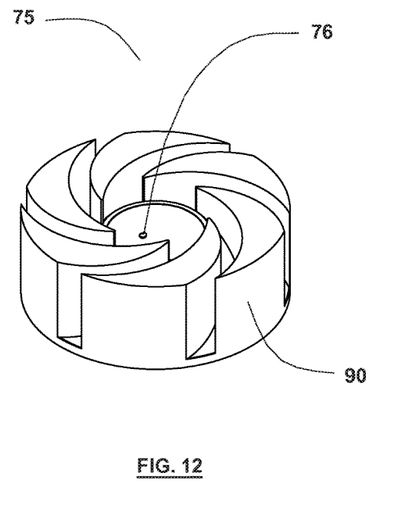

FIG. 11 and 12 are top and isometric views, respectively, of an embodiment of an impeller. Because impeller 75 is precision balanced and is a high efficiency impeller operating near its Best Efficiency Point (BEP), radial loads acting on impeller 75 are kept to a minimum of less than 0.5 N under conditions suitable for a ventricular assist device (VAD). In the embodiment shown, low radial loads, low coefficient of friction contact points, and low sliding speed results in low heat generation. For example, the radial mechanical contact bearing system may result in heat generation less than 0.5 watts. In addition to low heat generation, the bearing system allows a large radial clearance 78 between the inside bore of impeller 75 and the bearing surface 65 of diaphragm 60. In some embodiments, the radial clearance is equal to 0.005 inches or greater. A large radial clearance allows for improved continuous flushing of the radial clearance 78 with blood due the pressure differential between the underside of impeller 75 and pump inlet 20. The continuous flushing provides two benefits: (1) minimizing the formation and/or growth of blood clots; and (2) removing heat generated within the radial mechanical contact bearing, which both minimize blood trauma.

Figure 3:
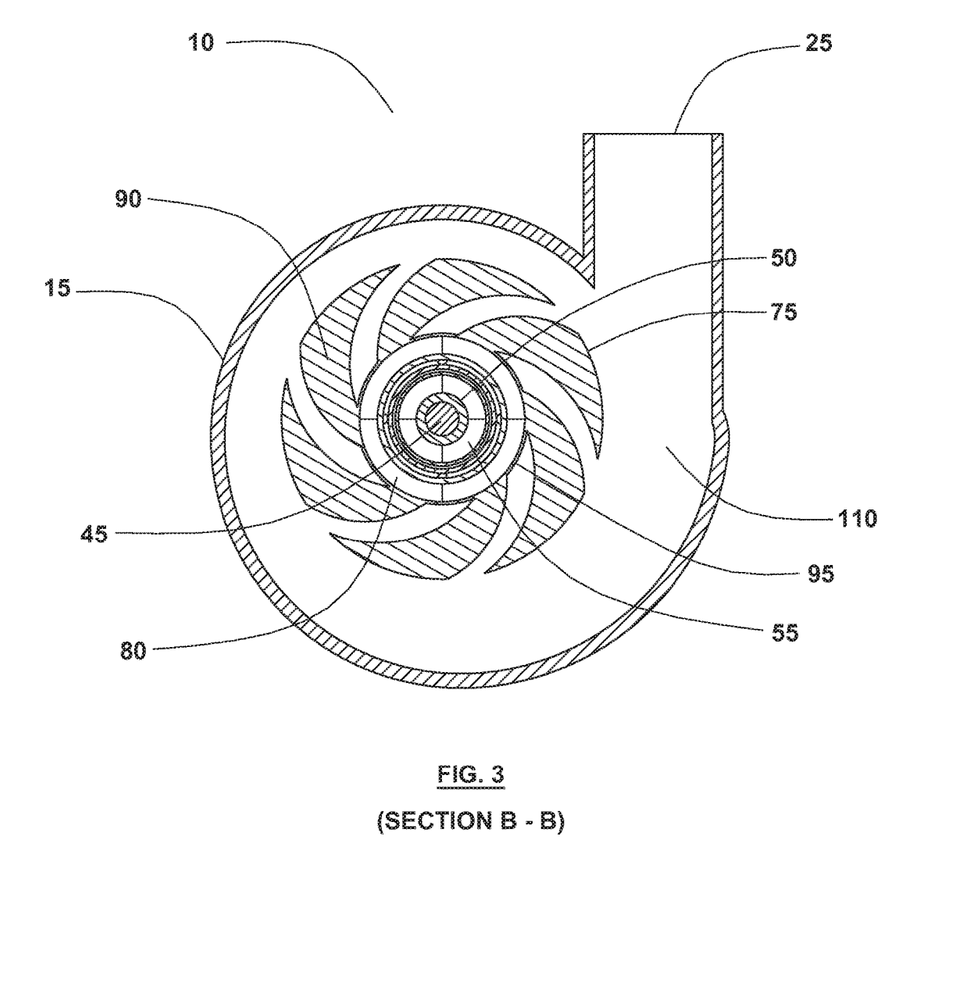
FIG. 3 is a cross-sectional top view of an illustrative embodiment of a pump thereof.

Line B-B of FIG. 2 passing through pump housing 15 indicates the plane from which the cross-section view in FIG. 3 is provided. FIG. 3 is a cross-sectional top view of an illustrative embodiment of pump 10. Impeller 75 is composed of an array of arc shaped segments 90 joined by central ring 95. Pump housing 15 has volute 110 feeding the outlet 25. In other embodiments, volute 110 could be omitted from pump housing 15 and outlet 25 could have any suitable orientation and shape. Pump housing 15 is designed in a manner where impeller 75, when rotated, pressures and moves fluid received from inlet 20 to outlet 25.

Permanent magnets 55 in hub 50 and permanent magnets 80 in central ring 95 of impeller 75 form a magnetic coupling between the impeller 75 and hub 50. In contrast to radial magnetic bearings that are arranged to repel each other, permanent magnets 55 and 80 are arranged so that they are attracted to each other. In order to further minimize radial loads, permanent magnets 55 and 80 provide a minimal magnetic coupling or just enough of a magnetic coupling to rotate impeller 75 under load. The attractive force of the magnetic coupling of permanent magnets 55 and 80 also provides axial restraint of impeller 75. For example, axial movement of impeller 75 may misalign permanent magnets 55 and 80. The attractive magnetic forces of permanent magnets 55 and 80 would restrain and re-align the magnets. Because of the magnetic forces caused by permanent magnets 55 and 80, axial movement of impeller 75 may cause axial force to be exerted on shaft 45 and hub 50 of motor 40, which is then transferred to bearing(s) (not shown) of motor 40.

Permanent magnets 80 may be sufficiently small in size that they have no impact on the main fluid flow paths of impeller 75, thereby allowing the design of impeller 75 to focus on fully optimizing pump efficiency. These benefits can allow pumping efficiencies of greater than 50% to be achieved.

Impeller 75 may be an open, pressure balanced type impeller to minimize axial thrust. Impeller 75 is considered to be open because there is no endplate on either side of arc shaped segments 90. Further, clearance 78 relieves pressure under impeller 75 and minimizes axial thrust during the rotation of impeller 75. However, other types of impellers may be suitable in other embodiments. Impeller 75 could be any other suitable blade shape, rotate in the opposite direction, or non-pressure balanced. For example, other suitable impellers may be semi-open type (i.e. end plate on one side of impeller) or closed type (i.e. end plate on both sides of impeller).

Referring to FIG. 4, the magnetic coupling transmits torque from shaft 45 of the motor 40 to impeller 75. Impeller radial support is provided by mechanical contact points 76. In the embodiment shown, permanent magnets 55 and 80 are radially distributed around hub 50 and impeller 75. The poles of permanent magnets 55 and 80 are arranged to attract to each other. The attractive force of the magnetic coupling of permanent magnets 55 and 80 provides axial restraint of impeller 75. While permanent magnets 55 and 80 are shown as arc shaped like quadrants of a cylinder in FIG. 3, it should be recognized that permanent magnets 55 and 80 may be shaped in a variety of different manners to provide the magnetic coupling. For example, one or more ring shaped magnets polarized with arc shaped magnetic regions, square/rectangular shaped, rod shaped, disc shaped, or the like may be utilized. In the magnetic coupling arrangement shown, permanent magnets 80 are shown in the internal portion of impeller 75. Internal magnetic couplings, similar to the arrangement shown, can be more efficient than face or external type magnetic couplings that place the magnets in the blades of an impeller or rotor because they have a smaller diameter and less eddy current losses. Diaphragm 60, intermediate the coupling, is non-ferromagnetic and/or non-electrically conductive to minimize eddy current losses. For example, couplings with non-electrically conducting diaphragms such as bio-compatible ceramic, glass, or the like, would exhibit less eddy current losses than those with electrically conducting diaphragms.

Figure 8:
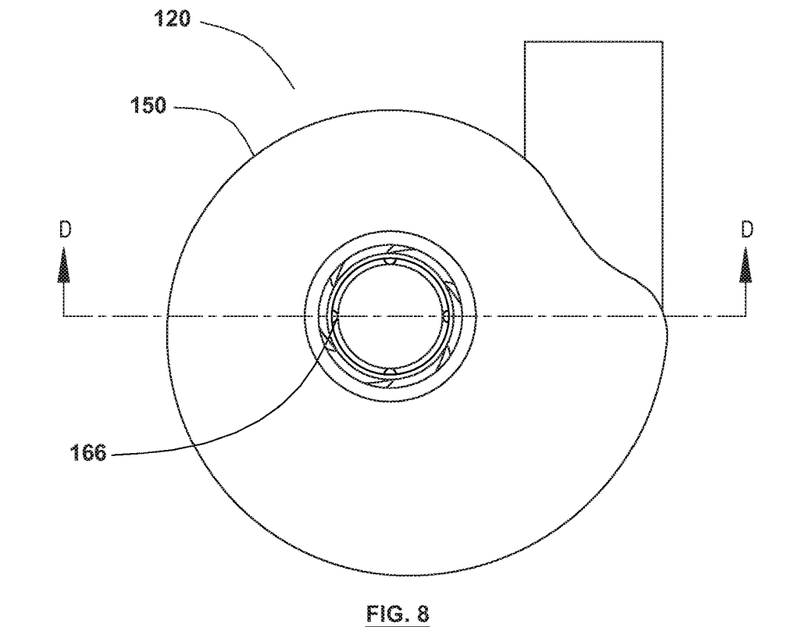
FIG. 8 is a top view of an illustrative embodiment of a pump.
Figure 9:
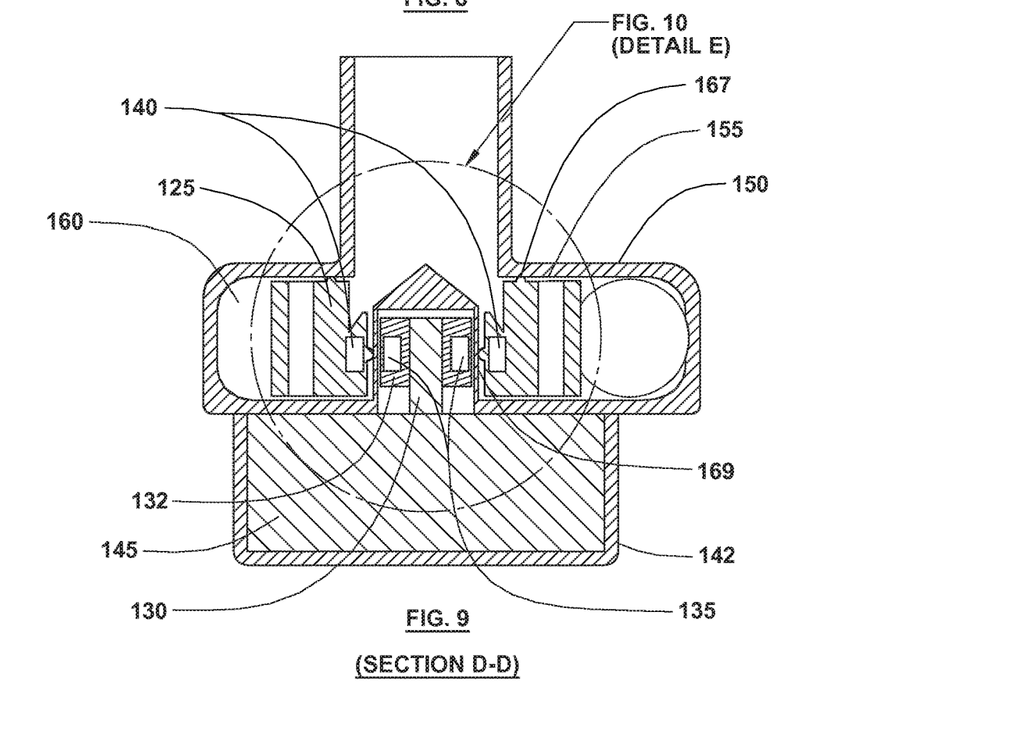
FIG. 9 is a cross-sectional side view of an illustrative embodiment of a pump with a radial and axial mechanical bearing.

FIG. 8 is a top view of an illustrative embodiment of pump 120. Line D-D passing through pump housing 150 indicates the plane from which the cross-sectional view in FIG. 9 is provided. FIG. 9 is a cross-sectional side view of an illustrative embodiment of pump 120. Similar to the embodiment shown in FIG. 2, pump 120 provides pump housing 150, impeller 125, shaft 130, hub 132, permanent magnets 135 and 140, motor housing 142, motor 145, impeller chamber 160, and cylindrical bearing surface 169 which all provide a similar function to the components discussed previously. These common elements may operate in substantially the same manner as previously described. The substantial differences in the embodiments are discussed below.

Figure 10:
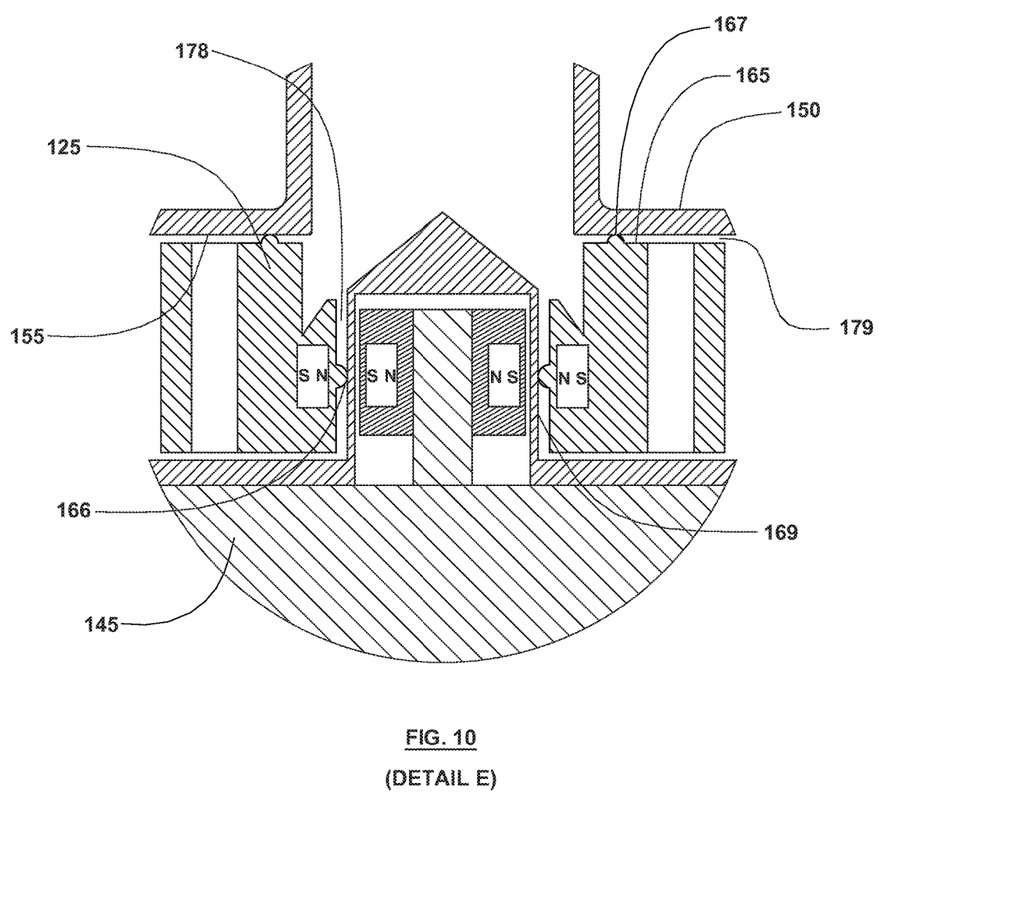
FIG. 10 is a close up cross-sectional view of an area of an illustrative embodiment of a pump thereof.
Figure 13:
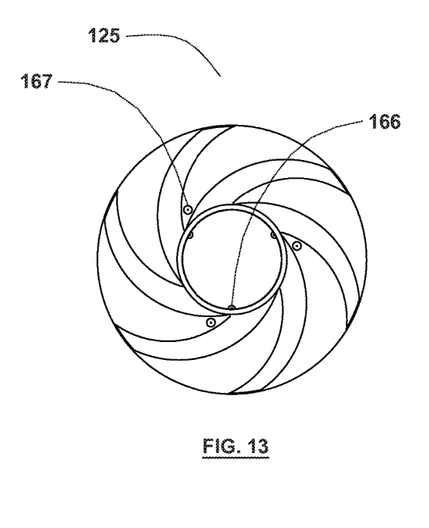
FIG. 13 and 14 are top and isometric views, respectively, of an illustrative embodiment of an impeller with a radial and axial mechanical bearing.
Figure 14:
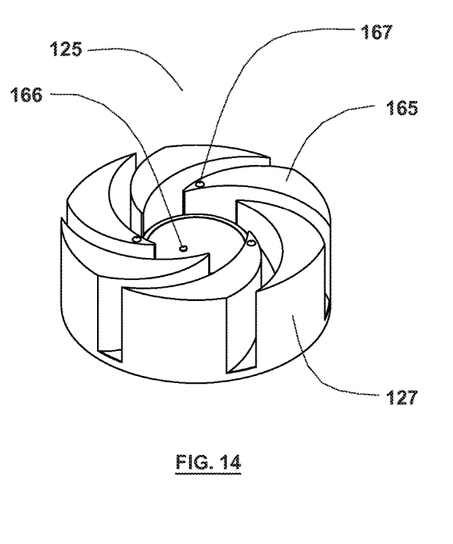

FIG. 10 is a close up cross-sectional view of an area E (see FIG. 9) of an illustrative embodiment of pump 120. In some embodiments of a bearing system, one or more top surfaces 165 of impeller 125 may include contact points 167 to provide axial restraint of the impeller 125. Contact points 167 may be referred to as axial contact points since axial loads are supported by these contact points. FIGS. 13 and 14 are top and isometric views, respectively, of impeller 125. Top surfaces 165 of impeller 125 provide one or more contact points 167 that may contact a bearing surface 155 of pump housing 150. While top surfaces 165 may be referred to as a singular "top surface" herein, it will be recognized that a "top surface" is not limited to a single surface and may collectively refer to all or a combination of one or more top surfaces provided by each arc shaped segment of impeller 125. While the embodiments shown provide three contact points 167, other embodiments may provide more than three contact points. Contact points 167 may be semi-spherically shaped, semi-ellipsoid shaped, flat shaped, or the like. Contact points 167 may be nonconforming or conforming. In some embodiments, the shape of contact points 167 matches the contour of bearing surface 155 of pump housing 150. The bearing surface 155 of pump housing 150 may be coated with a biocompatible low friction coating, such as Diamond Like Carbon (DLC) or the like. Contact points 167 may also be coated with a biocompatible low friction coating, such as Diamond Like Carbon (DLC) or the like. In some embodiments, the contact points 167 have a sliding Coefficient of Friction (COF) of 0.15 or less. The low friction coatings utilized on bearing surface 155 and contact points 167 lowers the amount of heat generated by friction. In other embodiments, bearing surface 155 and contact points 167 may be made from a hard biocompatible ceramic material such as aluminum oxide, zirconium dioxide, silicon carbide, or silicon nitride.

Because radial clearance 178 may be large enough to substantially relieve pressure under impeller 125, axial loads are kept to a minimum. For example, in the embodiment shown an axial load of less than 0.5 N at each contact point may be achieved. The combination of low axial loads, low coefficient of friction contact points, and low sliding speeds results in low heat generation by the axial mechanical contact bearing system. For example, the axial mechanical contact bearing system may result in heat generation less than 0.5 watts. By using the axial mechanical contact bearing, large axial clearance 179 equal to 0.005 inches or greater may be used between the top surfaces 165 of impeller 125 and the bearing surface 155 of pump housing 150. This allows for improved continuous flushing of the axial clearance 179 with blood due to the centrifugal action of impeller 125. The continuous flushing provides two benefits: (1) minimizing the formation and/or growth of blood clots; and (2) removing heat generated within the axial mechanical contact bearing, which both minimize blood trauma.

Implementations described herein are included to demonstrate particular aspects of the present disclosure. It should be appreciated by those of skill in the art that the implementations described herein merely represent exemplary implementation of the disclosure. Those of ordinary skill in the art should, in light of the present disclosure, appreciate that many changes can be made in the specific implementations described and still obtain a like or similar result without departing from the spirit and scope of the present disclosure. From the foregoing description, one of ordinary skill in the art can easily ascertain the essential characteristics of this disclosure, and without departing from the spirit and scope thereof, can make various changes and modifications to adapt the disclosure to various usages and conditions. The implementations described hereinabove are meant to be illustrative only and should not be taken as limiting of the scope of the disclosure.

What is claimed is:

1. A blood pump comprising:
   a pump housing providing an inlet, an outlet, and a bearing surface;
   an impeller housed in the pump housing and having a plurality of blades joined by a central ring;
   at least three contact protrusions circumferentially spaced on an internal surface of the impeller, wherein the impeller is radially supported by the contact protrusions sliding on the bearing surface; and
   a hub configured to rotate about an axis and comprising a first permanent magnet, wherein the impeller comprises a second permanent magnet located within the central ring, the first permanent magnet and the second permanent magnet overlapping each other in a direction of the axis and forming a radial magnetic coupling to transmit torque from the hub to the impeller;
   wherein a first portion of at least one of the plurality of blades defines a maximum height of the plurality of blades that is greater than or equal to heights of all other portions of the plurality of blades, as measured in a direction that is parallel to the axis;
   wherein each of the contact protrusions is axially between a top end of the first portion and a bottom end of the first portion, the bottom end being axially opposite the top end;
   wherein the radial magnetic coupling is axially between the top end of the first portion and the bottom end of the first portion;
   wherein a topmost extent of the plurality of blades is axially closer to the inlet in a direction of the axis than is (a) a topmost extent of each of the contact protrusions and the radial magnetic coupling and (b) a bottom of the plurality of blades;
   wherein at least a portion of the inlet extends along the axis and is positioned on a side of the impeller that is axially opposite the bottom of the plurality of blades.

2. The blood pump of claim 1, wherein said contact protrusions are semi-spherically shaped, semi-ellipsoid shaped, or concave shaped.

3. The blood pump of claim 1, further comprising:
   a motor housing, wherein the motor housing houses a motor; and wherein the magnetic coupling causes the impeller to rotate when the motor rotates, and said magnetic coupling supports the impeller axially.

4. The blood pump of claim 1 further comprising:
   an impeller chamber defined by the pump housing, wherein the impeller is housed in the impeller chamber; and
   a motor housing defining a motor chamber, wherein a motor is housed in the motor chamber; wherein the bearing surface separates the motor chamber and the impeller chamber.

5. The blood pump of claim 1, wherein the bearing surface and/or the contact protrusions of the impeller are coated with Diamond Like Carbon (DLC).

6. The blood pump of claim 1, wherein the radial contact protrusions have a sliding coefficient of friction of 0.15 or less.

7. The blood pump of claim 1, wherein the bearing surface is aluminum oxide, zirconium dioxide, silicon carbide, or silicon nitride.

8. The blood pump of claim 1, wherein the contact protrusions are aluminum oxide, zirconium dioxide, silicon carbide, or silicon nitride.

9. The blood pump of claim 1, wherein a radial load acting on any one of said contact protrusions is 0.5 N or less.

10. The blood pump of claim 1, wherein a total mechanical power consumed by said contact protrusions is 0.5 watts or less.

11. The blood pump of claim 1, wherein the impeller is an open pressure balanced type impeller that minimizes axial thrust during operation of the blood pump.

12. The blood pump of claim 1, wherein a clearance between the bearing surface and the internal surface of the impeller is 0.005 inches or greater.

13. The blood pump of claim 1, further comprising at least three axial contact protrusions positioned on top surfaces of blades of the impeller for axial support of the impeller.

14. The blood pump of claim 13, wherein the axial contact protrusions are semi-spherically shaped, semi-ellipsoid shaped, or flat shaped.

15. The blood pump of claim 13, wherein the axial contact protrusions slide on an inside surface of the pump housing.

16. The blood pump of claim 15, wherein the inside surface of the pump housing and/or axial contact protrusions are coated with Diamond Like Carbon (DLC).

17. The blood pump of claim 15, wherein the axial contact protrusions have a sliding coefficient of friction of 0.15 or less.

18. The blood pump of claim 15, wherein the inside surface of the pump housing is aluminum oxide, zirconium dioxide, silicon carbide, or silicon nitride.

19. The blood pump of claim 13, wherein the axial contact protrusions are aluminum oxide, zirconium dioxide, silicon carbide, or silicon nitride.

20. The blood pump of claim 13, wherein an axial load acting on any one of said axial contact protrusions is 0.5 N or less.

21. The blood pump of claim 13, wherein a total mechanical power consumed by said axial contact protrusions is 0.5 watts or less.

22. The blood pump of claim 13, wherein the impeller is an open pressure balanced type impeller that minimizes axial thrust during operation of the pump.

23. The blood pump of claim 15, wherein a clearance between said top surfaces of impeller and said inside surface of pump housing is 0.005 inches or greater.

\* \* \* \* \*